United States Patent [19]

Shoesmith, deceased

[11] Patent Number: Plant 5,531

[45] Date of Patent: Aug. 6, 1985

[54] CHRYSANTHEMUM PLANT NAMED POWERHOUSE

[75] Inventor: Leonard Shoesmith, deceased, late of Westfield, England, by May V. Shoesmith, executrix

[73] Assignee: Pan American Plant Company, Parrish, Fla.

[21] Appl. No.: 524,348

[22] Filed: Aug. 18, 1983

[51] Int. Cl.[3] ..... A01H 5/00

[52] U.S. Cl. ..... Plt./77

[58] Field of Search ..... Plt./77

*Primary Examiner*—Robert E. Bagwill

*Attorney, Agent, or Firm*—Schwartz, Jeffery, Schwaab, Mack, Blumenthal & Koch

[57] ABSTRACT

A new and distinct cultivar of chrysanthemum plant named Powerhouse characterized by its flat capitulum form and decorative capitulum type, white ray floret color, diameter of 70–100 mm. across face of the capitulum, medium pot plant height and compact growth habit, semi-upright branching patterns, and approximately nine week flowering time.

2 Drawing Figures

The present invention comprises a new and distinct cultivar of *Chrysanthemum morifolium,* Ramat., hereinafter referred to by the cultivar name Powerhouse.

Powerhouse is a product of a planned breeding program which had the objective of creating new chrysanthemum cultivars having decorative capitulum type, flat capitulum form, white ray floret color, approximately 9 week flowering time, and having the ability to produce commercially acceptable quality in year round pot mum programs. Such traits in combination were not present in previously available commercial cultivars.

Powerhouse was originated from a hybridization made in a controlled breeding program by or under the supervision of applicant in West Chicago, Ill., in 1976. Both the male and female parents are unknown at this time.

Powerhouse was discovered and selected as one flowering plant within the progeny of the cross by applicant in November, 1979 in a controlled environment in West Chicago, Ill., and given the code name K-25.

The first act of asexual reproduction of Powerhouse was accomplished when vegetative cuttings were taken from the initial selection in February, 1978 by or under the supervision of applicant in West Chicago, Ill. Horticultural examination of selected units was initiated in May, 1978, and that and subsequent examinations, in which the variety was recorded P7-457K-W, have demonstrated that the combination of characteristics as herein disclosed for Powerhouse are firmly fixed and are retained through successive generations of asexual reproduction.

Powerhouse has not been observed under all possible environmental conditions. The phenotype may vary significantly with variations in environment such as temperature, light intensity, and day length. The following observations, measurements and comparisons describe plants grown in West Chicago, Ill. and Parrish, Fla. under greenhouse conditions which approximate those generally used in commercial practice.

The following traits have been repeatedly observed and are determined to be basic characteristics of Powerhouse, which in combination distinguish this chrysanthemum as a new and distinct cultivar:

1. Flat capitulum form.
2. Decorative capitulum type.

3. White ray floret color.
4. Diameter of 70–100 mm. across the face of the capitulum.
5. Medium pot plant height of 300 mm. from edge of the pot.
6. Semi-upright branching pattern.
7. A compact growth habit, with strong stems.
8. Nine (9) week flowering time.

Of the many commercial cultivars known to the present inventor, the most similar in comparison to Powerhouse is Windsong, disclosed in U.S. Plant Pat. No. 3,358. In comparison to Windsong, Powerhouse has stronger stems, a more compact habit, a more yellowish white flower center, and is 3–5 days later in flowering. The white color, capitulum form and capitulum type are similar to those same characteristics of Windsong.

The accompanying photographic drawings show typical inflorescence and foliage characteristics of Powerhouse, with colors being as nearly true as possible with illustrations of this type. Sheet 1 is a color photograph of Powerhouse. Sheet 2 is a print of the underside of typical leaves of Powerhouse, taken at various states of growth.

In the following description color references are made to The Royal Horticultural Society Colour Chart. The color values were determined between 3:30 and 4:30 P.M. on Nov. 16, 1982 under 2000–3000 foot candles of light intensity at Parrish, Fla.

Classification:

*Botanical.*—*Chrysanthemum morifolium,* Ramat., CV Powerhouse.

*Commercial.*—Decorative pot mum.

I. INFLORESCENCE

A. Capitulum:

*Form.*—Flat.

*Type.*—Decorative.

*Diameter across face.*—70–100 mm.

B. Corolla of ray florets:

*Color (general tonality from a distance of three meters)*: White, with yellowish white centers.

*Color (abaxial).*—155D.

*Color (adaxial).*—155D.

C. Corolla of disc florets:

*Color (mature).*—Yellow.

*Color (immature).*—Lime green.

D. Reproductive organs:

*Androecium.*—Present disc florets only.

*Gynoecium.*—Present birth ray and disc florets; numerous.

II. PLANT

A. General appearance:

*Height.*—From edge of pot, about 300 mm.

B. Foliage:

*Color (abaxial).*—147B.

*Color (adaxial).*—147A.

*Shape.—Deeply lobed and slightly serrated.*

I claim:

1. A new and distinct cultivar of chrysanthemum plant named Powerhouse, as described and illustrated, and particularly characterized by its flat capitulum form and decorative capitulum type; white ray floret color; diameter of 70–100 mm. across face of the capitulum; medium pot plant height and compact growth habit; semi-upright branching pattern, and approximately nine week flowering time.

* * * * *

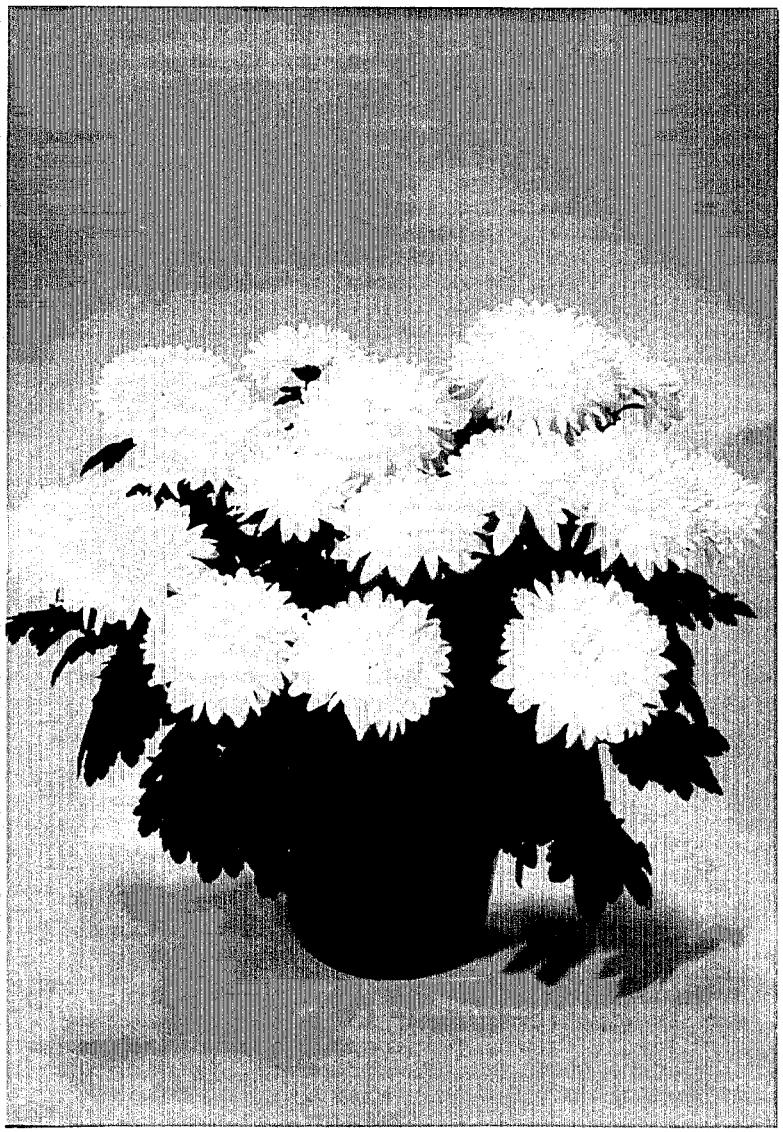

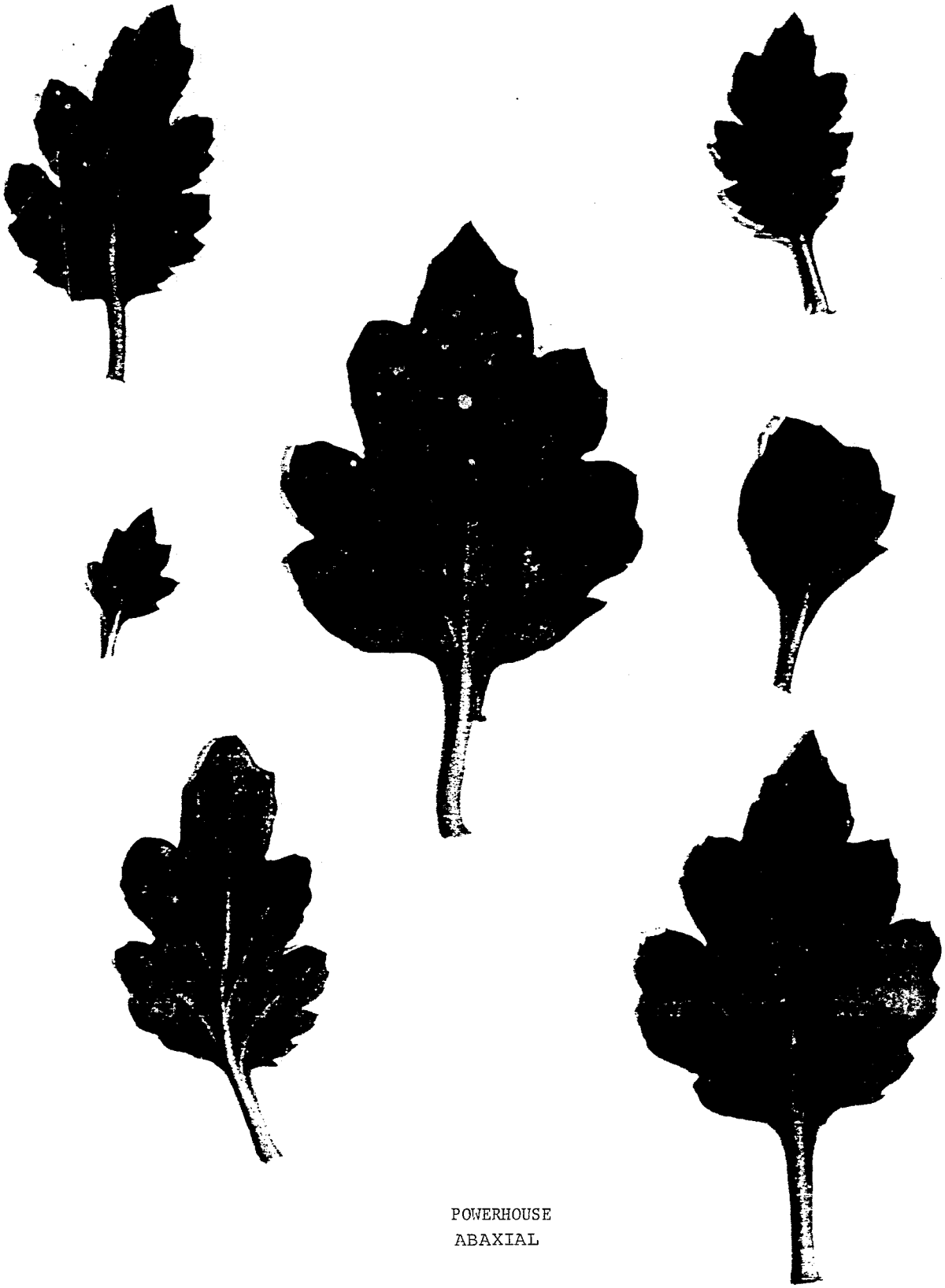
POWERHOUSE
ABAXIAL